US006939968B2

(12) United States Patent
Vrudhula et al.

(10) Patent No.: US 6,939,968 B2
(45) Date of Patent: Sep. 6, 2005

(54) ATROPISOMERS OF 3-SUBSTITUTED-4-ARYLQUINOLIN-2-ONE DERIVATIVES

(75) Inventors: Vivekananda M. Vrudhula, Killingworth, CT (US); Valentin Kala Gribkoff, Wallingford, CT (US); Bireshwar Dasgupta, Middletown, CT (US); Christopher G. Boissard, Northford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 57 days.

(21) Appl. No.: 10/739,449

(22) Filed: Dec. 17, 2003

(65) Prior Publication Data

US 2004/0147749 A1 Jul. 29, 2004

Related U.S. Application Data

(60) Provisional application No. 60/436,160, filed on Dec. 23, 2002.

(51) Int. Cl.[7] .................... C07D 215/16; C07D 215/20; A61K 31/47

(52) U.S. Cl. ........................ 546/156; 546/157; 514/312

(58) Field of Search ................................ 546/156, 157; 514/312

(56) References Cited

U.S. PATENT DOCUMENTS

| | | | |
|---|---|---|---|
| 5,892,045 A | 4/1999 | Sit et al. | |
| 5,922,735 A | 7/1999 | Sit et al. | |
| 6,184,231 B1 * | 2/2001 | Hewawasam et al. | 514/312 |
| 6,353,119 B1 * | 3/2002 | Crispino et al. | 546/156 |

* cited by examiner

*Primary Examiner*—D. Margaret Seaman
(74) *Attorney, Agent, or Firm*—James Epperson

(57) ABSTRACT

Atropisomers of 3-substituted-4-arylquinolin-2-one derivatives having the general formula

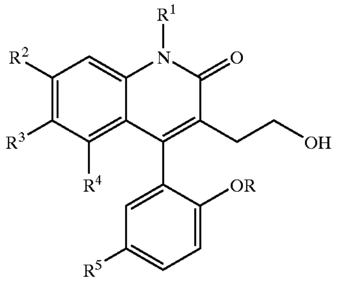

wherein R, $R^1$, $R^2$, $R^3$, $R^4$ and $R^5$, are as defined herein, or a non-toxic pharmaceutically acceptable salt, solvate or prodrug thereof. The atropisomers can modulate the large conductance calcium-activated $K^+$ channels and are useful in the treatment of disorders which are responsive to the opening of the potassium channels. In addition, the atropisomers can be stable, i.e., do not interconvert, for periods of up to one month, or more.

20 Claims, 4 Drawing Sheets

ATROPISOMERS OF 3-SUBSTITUTED-4-ARYLQUINOLIN-2-ONE DERIVATIVES

REFERENCE TO RELATED APPLICATIONS

This application claims the benefit of U.S. provisional application No. 60/436,160 filed Dec. 23, 2002.

BACKGROUND OF THE INVENTION

Potassium channels are transmembrane proteins which are ubiquitously expressed in mammalian cells and represent one of the largest and the most diverse group of ion channels from a molecular perspective. Potassium channels play a key role in regulation of cell membrane potential and modulation of cell excitability. Potassium channels are largely regulated by voltage, cell metabolism, calcium and receptor mediated processes. [Cook, N. S., Trends in Pharmacol. Sciences (1988), 9, 21; and Quast, U., et al., Trends in Pharmacol. Sciences (1989), 10, 431]. Calcium-activated potassium ($K_{ca}$) channels are a diverse group of ion channels that share a dependence on intracellular calcium ions for activity. The activity of $K_{ca}$ channels is regulated by intracellular [$Ca^{2+}$], membrane potential and phosphorylation. On the basis of their single-channel conductances in symmetrical $K^+$ solutions, $K_{ca}$ channels are divided into three subclasses: large conductance (also referred to in the art as "BK" or "Maxi-K"), having a conductance of greater than about 150 picosemens ("pS"); intermediate conductance, having a conductance of about 50–150 pS; and small conductance, having a conductance of less than about 50 pS. Large-conductance calcium-activated potassium channels are present in many excitable cells including neurons, cardiac cells and various types of smooth muscle cells. [Singer, J. et al., Pflugers Archiv. (1987) 408,98; Baro, I., et al., Pflugers Archiv. (1989) 414 (Suppl. 1), S168; and Ahmed, F. et al., Br. J. Pharmacol. (1984) 83, 227].

Potassium ions play a dominant role in controlling the resting membrane potential in most excitable cells and maintain the transmembrane voltage near the $K^+$ equilibrium potential ("$E_k$") of about −90 milliVolts ("mV"). It has been shown that opening of potassium channels shift the cell membrane potential towards the $E_k$, resulting in hyperpolarization of the cell. [Cook, N. S., Trends in Pharmacol. Sciences (1988), 9, 21]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells, as well as other types of cells, e.g., cardiac cells. [Xu, W., Liu, Y., Wang, S., McDonald, T., Van Eyk, J. E., Sidor, A., and O'Rourke, B. (2002) Cytoprotective Role of $Ca^{2+}$-activated $K^+$ Channels in the Cardiac Inner Mitochondrial Membrane. *Science* 298, 1029–1033].

A variety of synthetic and naturally occurring compounds with BK opening activity have been reported. Of particular interest are 4-aryl-3-hydroxyquinolin-2-one derivatives disclosed, for example, in U.S. Pat. No. 5,892,045, issued Apr. 6, 1999, U.S. Pat. No. 5,922,735, issued Jul. 13, 1999, U.S. Pat. No. 6,353,119, issued Mar. 5, 2002.

Despite the advances in the art made possible by the 4-aryl-3-hydroxyquinolin-2 one derivatives noted above, further advances are desired in the class of compounds capable of modulating potassium channels, in particular, large-conductance calcium-activated potassium channels. Desirably, such compounds would be useful in treating conditions arising from dysfunction of cellular membrane polarization and conductance.

SUMMARY OF THE INVENTION

In accordance with the present invention, atropisomers of 3-substituted-4-arylquinolin-2-one derivatives are provided.

The atropisomers are compounds having the general formula

I

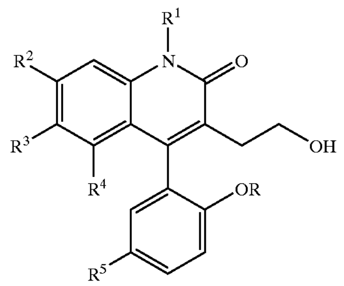

wherein R, $R^1$, $R^2$, $R^3$, $R^4$ and $R^5$ are as defined below, or non-toxic pharmaceutically acceptable salt, solvate or prodrug thereof; characterized in that the compounds are atropisomerically enriched, and preferably, substantially pure with respect to one atropisomer.

By virtue of the present invention, it is now possible to provide stable atropisomers of 3-substituted-4-arylquinolin-2-one derivatives. Quite surprisingly, in accordance with the present invention, it has been found that the atropisomers do not readily interconvert, even after extended periods, e.g., 30 days or more. As a result, pharmaceutical compositions can be tailored to be enriched in the atropisomer most effective for treating the targeted condition.

The present invention also provides pharmaceutical compositions comprising the atropisomers of 3-substituted-4-arylquinolin-2-one derivatives and methods for the treatment of conditions sensitive to potassium channel opening activity such as, for example, ischemia, stroke, convulsions, epilepsy, asthma, irritable bowel syndrome, migraine, traumatic brain injury, spinal cord injury, sexual dysfunction and urinary incontinence.

DETAILED DESCRIPTION OF THE INVENTION

Figure 1:
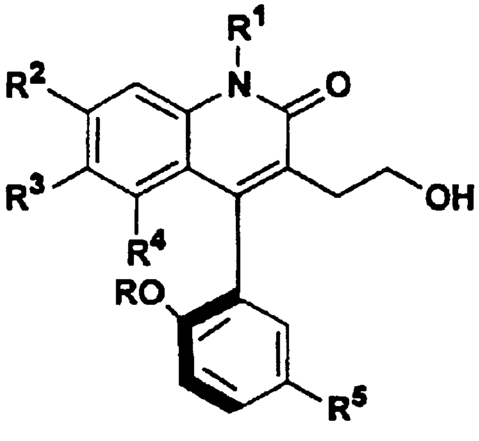
FIG. 1 shows a structural representation of two atropisomers in accordance with the present invention.

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture.

The terms "racemic mixture" and "racemate" refer to an equimolar mixture of two enantiomeric species, devoid of optical activity. In addition, as used herein, the terms "racemic mixture" and "racemate" are intended to include equimolar mixtures of the two atropisomers.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "atropisomer" refers to a stereoisomer resulting from restricted rotation about single bonds where the rotation barrier is high enough to permit isolation of the isomeric species. Typically, rotation about the single bond in the molecule is prevented, or greatly slowed, as a result of steric interactions with other parts of the molecule and the substituents at both ends of the single bond are unsymmetrical.

The term "atropisomerically enriched" means that the compound, i.e., mixture of atropisomers, comprises a greater proportion or percentage of one of the atropisomers of the compound, in relation to the other atropisomer, i.e., greater than 50 mole %.

The term "substantially pure" means that the compound, i.e., mixture of atropisomers, comprises at least 90 mole %, preferably at least 95 mole % and more preferably at least 99 mole % of one atropisomer.

The term "substantially free" means that the compound comprises less than 10 mole %, preferably less than 5 mole % and more preferably less than 1 mole % of one atropisomer.

The terms "interconversion" and "interconvert" means the conversion of an atropisomerically enriched compound to a racemic mixture.

The terms "stable" and "stability" mean that an atropisomerically enriched compound does not interconvert at room temperature, i.e., 25° C., in solution form, e.g., a 3 milligram per milliliter ("mg/mL") solution in ethanol, for a period of at least about 1 day, preferably at least about 10 days and more preferably at least about 30 days. In testing the stability in accordance with the present invention, solvents other than ethanol, e.g., 2-propanol, or mixtures of alcoholic solvents with cosolvents, e.g., toluene, can be used. When the compounds of the present invention are present in solid form, i.e., not dissolved or dispersed in a liquid, they are often even more resistant to interconversion than when in a liquid form.

The term "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445. Suitable inorganic bases such as alkali and alkaline earth metal bases include metallic cations such as sodium, potassium, magnesium, calcium and the like. The compounds of the present invention are useful in the form of the free base or acid or in the form of a pharmaceutically acceptable salt thereof. All forms are within the scope of the invention.

The term "halogen" as used herein and in the claims is intended to include fluorine, bromine, chlorine and iodine while the term "halide" is intended to include fluoride, bromide, chloride and iodide anion.

The term "therapeutically effective amount" means the total amount of each active component that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of Formula I, and include prodrugs, pharmaceutically acceptable salts, and solvates, e.g. hydrates. Similarly, reference to intermediates, whether or not they themselves are claimed, is meant to embrace their salts, and solvates, where the context so permits. References to the compound of Formula I also include the compounds of Formula II and III.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, $18^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable risk/benefit ratio.

The term "pharmaceutically acceptable prodrugs" as used herein means those prodrugs of the compounds useful according to the present invention which are, within the scope of sound medical judgment, suitable for use in contact with the tissues of humans and lower animals without undue toxicity, irritation, allergic response, and the like, commensurate with a reasonable risk/benefit ratio, and effective for their intended use, as well as zwitterionic forms, where possible, of the compounds of the invention.

The term "prodrugs", as the term is used herein, are intended to include any covalently bonded carriers which release an active parent drug of the present invention in vivo when such prodrug is administered to a patient. Since prodrugs are known to enhance numerous desirable qualities of pharmaceuticals (i.e., solubility, bioavailability, manufacturing, etc.) the compounds of the present invention may be delivered in prodrug form. Thus, the skilled artisan will appreciate that the present invention encompasses prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to form the parent compound. The transformation in vivo may be, for example, as the result of some metabolic process, such as chemical or enzymatic hydrolysis of a carboxylic, phosphoric or sulphate ester, or reduction or oxidation of a susceptible functionality. Prodrugs include compounds of the present invention wherein a hydroxy, amino, or sulfhydryl group is bonded to any group that, when the prodrug of the present invention is administered to a patient, it cleaves to form a free hydroxyl, free amino, or free sulfydryl group, respectively. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups can act as prodrugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p.309–396, 1985; A Textbook of Drug Design and Development, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The 3-substituted-4-arylquinolin-2-one derivatives of the present invention are atropisomerically enriched compounds having the formula

I

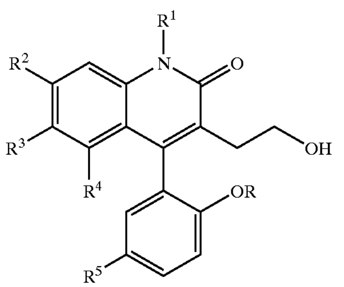

wherein R and $R^1$ each are independently hydrogen or methyl;

$R^2$, $R^3$ and $R^4$ each are independently hydrogen, halogen, nitro or trifluoromethyl, provided $R^2$, $R^3$ and $R^4$ are not all hydrogen; and a nontoxic pharmaceutically acceptable salt, solvate or prodrug thereof.

In one preferred aspect of the invention, $R^1$ is hydrogen. In another preferred aspect of the invention, $R^1$ is methyl. In still yet another aspect of the invention, R, $R^2$ and $R^4$ are hydrogen, $R^3$ is trifluoromethyl and $R^5$ is chloro.

One atropisomer of the invention can be represented by the formula:

II

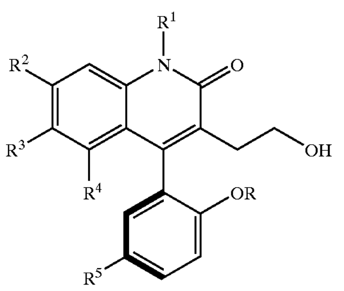

For purposes of describing the present invention, the above structure is arbitrarily referred to herein as the (−)atropisomer or atropisomer (A). The bold section of the phenyl ring on the 4 position of the quinolinone denotes the partial rotation of the phenyl ring out of the plane in which the quinolinone is situated.

Another atropisomer of the invention can be represented by the formula:

(III)

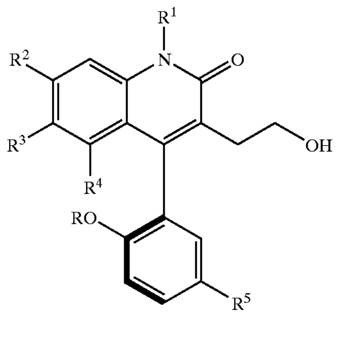

For purposes of describing the present invention, the above structure is arbitrarily referred to herein as the (+) atropisomer or atropisomer (B).

Preferred compounds for use in the method of this invention include the compounds of Formula I listed below:

(1) 4-(5-chloro-2-hydroxyphenyl)-1-methyl-3-(2-hydroxyethyl)-6-(trifluoromethyl)-2(1H)-quinolinone;

(2) 4-(5-chloro-2-hydroxyphenyl)-1-methyl-3-(2-hydroxyethyl)-7-trifluoromethyl-2(1H)-quinollinone;

(3) 4-(5-chloro-2-hydroxyphenyl)-3-(2-hydroxyethyl)-6-(trifluoromethyl)-2(1H)-quinolinone; and (4) 4-(5-chloro-2-hydroxyphenyl)-3-(2-hydroxyethyl)-7-(trifluoromethyl)-2(1H)-quinolinone.

The compounds of Formula I may be prepared by various procedures known to those skilled in the art, such as, for example, disclosed in U.S. Pat. Nos. 6,184,231, issued Feb. 6, 2001 and U.S. Pat. No. 6,353,119, issued Mar. 5, 2002.

The following reaction scheme illustrates representative general procedures for the preparation of intermediates and methods for the preparation of compounds of Formula I according to this invention. It should also be evident to those skilled in the art that appropriate substitution of both the materials and methods disclosed herein will produce the examples illustrated below and those encompassed by the scope of this invention.

REACTION SCHEME 1

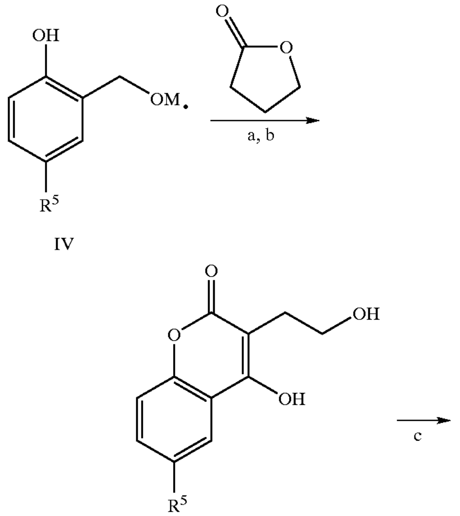

IV

V

-continued

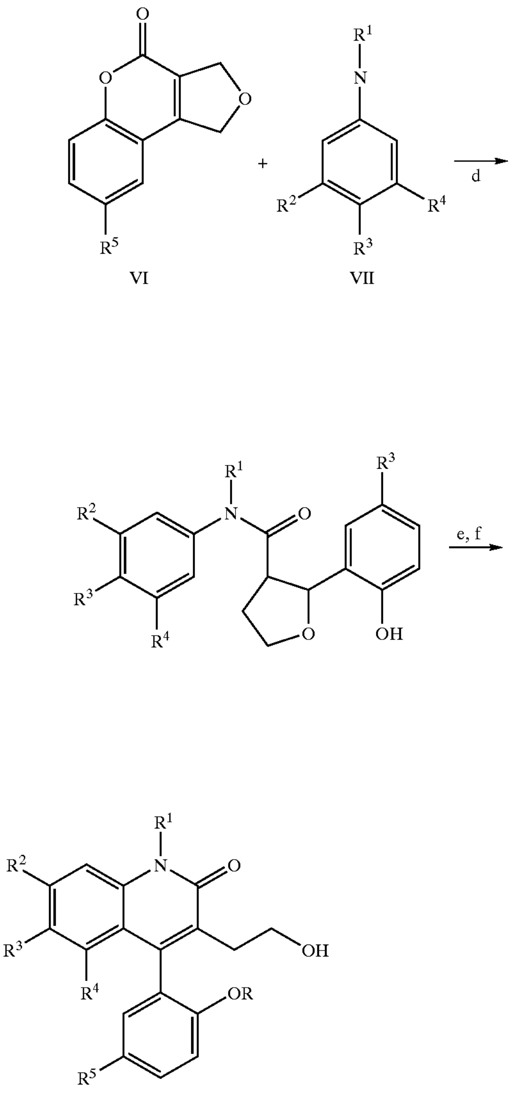

VI VII

I (a) LiHMDS/THF, -78° C. to RT
(b) 12N HCl
(c) pTSA, Toluene, reflux
(d) LiHMDS
(e) $(CH_3O)_2SO_2$, $K_2CO_3$
(f) hv, MeOH The preparation of racemic mixture of compounds of Formula I can be carried out by the reactions illustrated in Reaction Scheme 1. The coumarin compound of Formula V is preferably prepared by condensing γ-butyrolactone with the methyl ester of a substituted salicylic acid of Formula IV which is then readily cyclized with a catalytic amount of acid to produce the benzopyran-4-one of Formula VI. Treatment of compound VI with a substituted aniline of Forumla VII as illustrated in step (d) produced the dihydrofuran of Formula VIII which is then optionally methylated with a methylating agent such as dimethyl sulfate. The dihydrofuran of Formula VIII is then advantageously subjected to a photochemical cyclization in an inert organic solvent to afford the desired compound of Formula I.

A preferred reaction scheme for preparing the compounds of Formula I is set forth below:

REACTION SCHEME 2
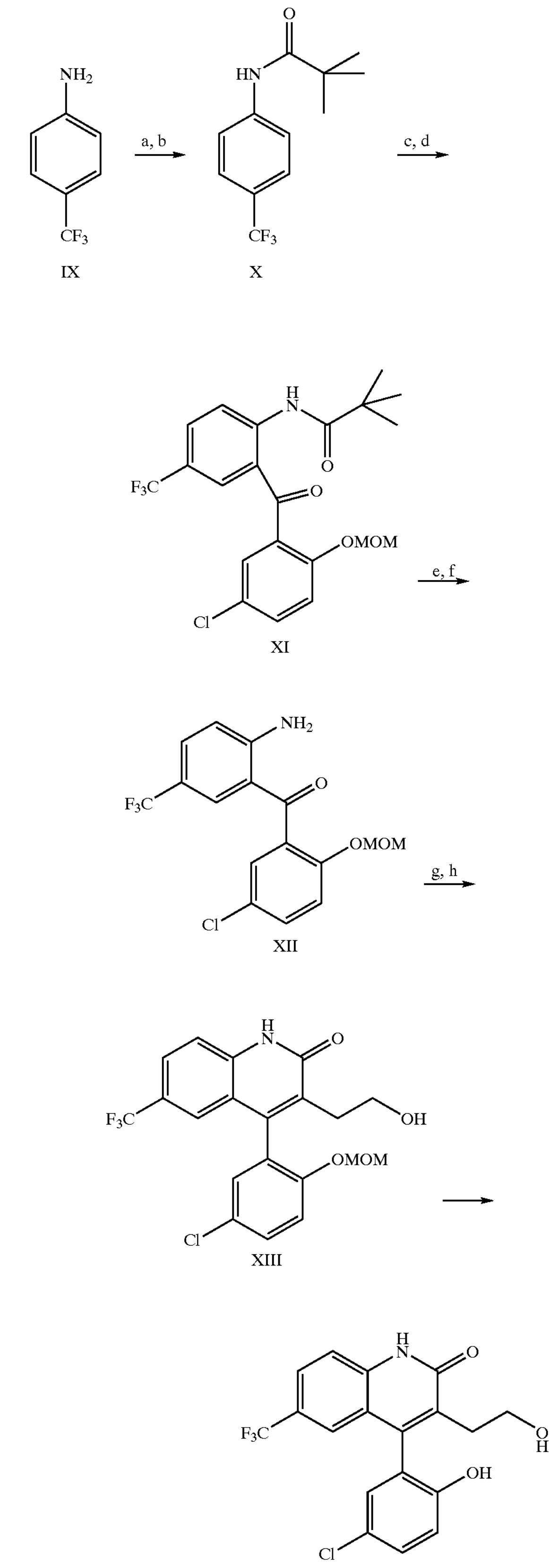
IX X XI XII XIII I
-continued
a) $Me_3COOMe$, THF
b) NaHMDS, 0-rt, 2 h
c) n-BuLi, -40–0° C.,
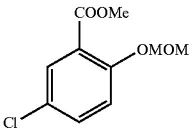
d) -78 to -40° C., 2 h
e) NaOH, EtOH,
f) 40° C., 1.5 h
g) 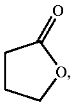, LiHMDS
h) 0-rt, 1 h, then $H_2O$, rt, 2 h
i) i-PrOH, HCl
j) 45° C., 3 h
Another preferred reaction scheme for preparing the compounds of Formula I is set forth below:
REACTION SCHEME 3
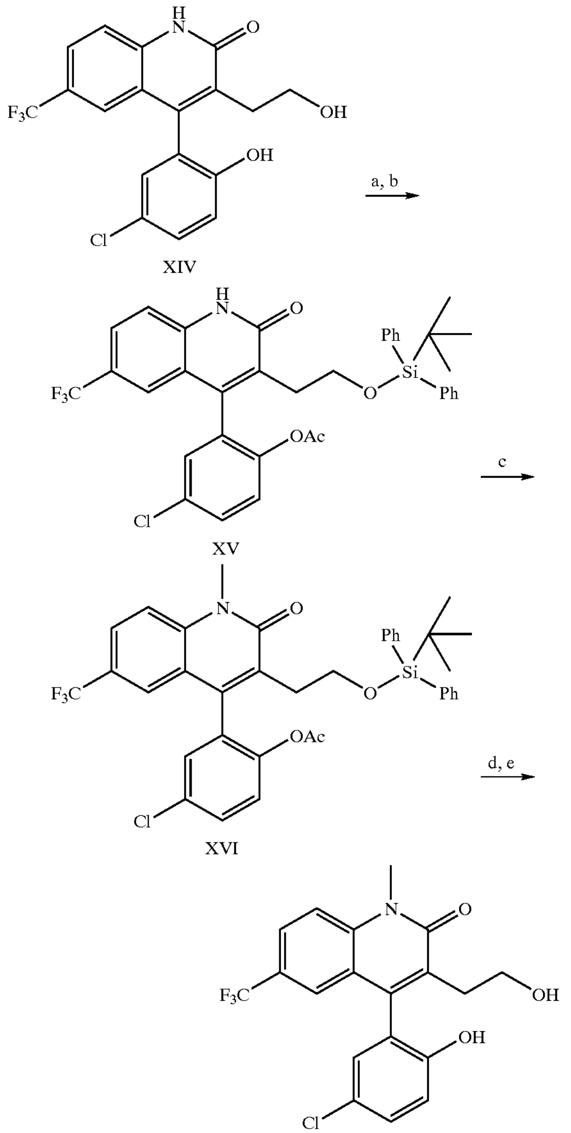
XIV XV XVI I -continued a) 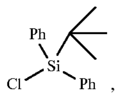 , DMF, imidazole, rt, 3h b) $Ac_2O$, $Et_3N$, $CH_2Cl_2$, 4h c) MeI, acetone, $K_2CO_3$, rt d) $LiOH{\bullet}H_2O$, EtOH, 18h, rt e)n-$Bu_4NF$, THF, 36h In accordance with the present invention, the reaction product containing the (−) atropisomer and (+) atropisomer can be resolved to provide a fraction enriched, and preferably substantially pure, with respect to one of the atropisomers. Preferably, the fraction containing the desired atropisomer, e.g., (−) atropisomer, is substantially free of the corresponding atropisomer, e.g., (+) atropisomer. Preferably, two fractions are provided: a first fraction enriched, and preferably substantially pure, with respect to the (−) atropisomer, and a second fraction enriched, and preferably substantially pure, with respect to the (+) atropisomer.

The particular method for resolving the mixture of atropisomers is not critical to the present invention. Any suitable method known to those skilled in the art can be employed, e.g., formation of ionic, diastereomeric salts (or coordination complexes) with chiral compounds and separation by fractional crystallization or other methods, formation of diastereomeric compounds with chiral derivatizing reagents, separation of the diastereomers, and conversion to the pure atropisomers, separation of the atropisomers directly under chiral conditions on a variety of matrices including supercritical chromatography and enzymatic hydrolysis. See, e.g., Stereochemistry of Carbon Compounds, supra; Lochmuller, C. H., (1975) J. Chromatogr., 113:(3) 283–302).

For example, diastereomeric salts can be formed by the reaction of enantiomerically pure chiral bases such as, for example, brucine, quinine, ephedrine, strychnine, α-methyl-β-phenylethylamine (amphetamine), and the like with compounds of the invention bearing acidic functionality, such as carboxylic acid and sulfonic acid. The diastereomeric salts may be induced to separate by fractional crystallization or ionic chromatography. For separation of the compounds of the invention bearing amine functionality, addition of chiral carboxylic or sulfonic acids, such as, for example, camphorsulfonic acid, tartaric acid, mandelic acid, or lactic acid can result in formation of the diastereomeric salts.

Alternatively, the racemic mixture of compounds to be resolved can be reacted with one enantiomer of a chiral compound to form a diastereomeric pair. For example, diastereomeric compounds can be formed by reacting the compounds of the invention with enantiomerically pure chiral derivatizing reagents, such as, for example, menthyl derivatives, followed by separation of the diastereomers and hydrolysis to yield the free, atropisomerically enriched compound. A preferred method of determining optical purity involves making chiral esters, such as a menthyl ester or Mosher ester, e.g., α-methoxy-α-(trifluoromethyl)phenyl acetate [Jacob III. (1982) J. Org. Chem. 47:4165], of the racemic mixture, and analyzing the nuclear magnetic resonance ("NMR") spectrum for the presence of the two atropisomeric diastereomers.

Alternatively, a racemic mixture of the two atropisomers can be separated by chromatography using a chiral stationary phase see, e.g., Chiral Liquid Chromatography; W. J. Lough, Ed. Chapman and Hall, New York, (1989); Okamoto, "Optical resolution of dihydropyridine enantiomers by high-performance liquid chromatography using phenylcarbamates of polysaccharides as a chiral stationary phase", J. of Chromatogr. 513:375–378, (1990). Atropisomers of the compounds of the invention can be separated and isolated by chromatography on chiral stationary phase, for example, with a Chiralpak AD column e.g., using a mobile phase containing: (a) 2-Propanol; and (b) hexane containing a small proportion (0.1–0.15%) of either trifluroacetic acid ("TFA") or diethyl amine ("DEA").

Alternatively, the primary alcohol group in the compounds of the invention could be esterified with a chiral carboxylic acid to form chiral esters which can undergo diastereoselective hydrolysis by an enzyme, e.g., esterase.

Characterization of the atropisomers can be accomplished by any suitable techniques known to those skilled in the art. Examples of suitable techniques include NMR spectroscopy, e.g., proton NMR or $C^{13}$ NMR, infared spectroscopy, ultraviolet spectroscopy, physical measurements, e.g., melting point, x-ray crystallography and chiral chromatography for enantiomeric purity. Generally, atropisomers can be distinguished by methods used to distinguish other chiral molecules with asymmetric carbon atoms, such as optical rotation and circular dichroism.

Quite surprisingly in accordance with the present invention, it has been found that the resolved atropisomers are stable. As a result, it is possible to provide compounds enriched, and preferably substanitally pure, with respect to the desired atropisomer which are resistent to interconversion to the racemic mixture. The ability to provide stable atropisomers is advantageous. For example, an atropisomer which is more active to treat a certain condition can be provided at dosages which may be substanitally less than a dosage of the racemic mixture having the same effectiveness, e.g., up to one-half less. Alternatively, a dosage which is the same as the dosage of the racemic mixture can be provided having enhanced effectiveness.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention. It is believed that certain compounds of Formula I can exist in two tautameric forms. It should be appreciated by those skilled in the art that when $R^1$ is hydrogen on the nitrogen atom adjacent to the carbonyl carbon atom, the quinoline ring can exist in an enol form. It is intended that both enolic tautomers of the compounds of Formula I are included within the scope of the present invention.

Openers of BK channels exert their cellular effects by increasing the open probability of these channels [Gribkoff, V. K., et al., Neuroscientist, 7:166–177 (2001); Gribkoff, V. K. et al., Adv. Pharmacol., 37:319–348 (1997); McKay, M. C., et al., J. Neurophysiol., 71: 1873–1882 (1994); and Olesen, S.-P., Exp. Opin. Invest. Drugs, 3: 1181–1188 (1994)]. This increase in the opening of individual BK channels collectively results in the hyperpolarization of cell membranes, particularly in depolarized cells, produced by significant increases in whole-cell BK-mediated conductance. Hyperpolarization, in turn, reduces the excitability of nerve and muscle cells, and decreases the open probability of voltage-dependent $Ca^{2+}$ channels, effectively lowering intracellular concentrations of this potentially harmful cation.

The ability of the compounds of the invention to open BK channels and increase whole-cell outward (K+) BK-mediated currents was assessed under voltage-clamp conditions by determining their ability to increase cloned mammalian (mSlo or hSlo) BK—mediated outward current heterologously expressed in Xenopus oocytes [Butler, A., et al., Science, 261: 221–224 (1993); Dworetzky, S. I., et al., Mol. Brain Res., 27: 189–193 (1994); Gribkoff, V. K., et al., Mol. Pharmacol., 50:206–217 (1996)]. The two BK constructs employed represent nearly structurally identical homologous proteins, and have proven to be pharmacologically indistinguishable in our tests. To isolate BK current from native (background, non-BK) current, the specific and potent BK channel-blocking toxin iberiotoxin (IBTX) [Galvez, A., et al., J. Biol. Chem., 265: 11083–11090 (1990)] was employed at a supramaximal concentration, e.g., 50–100 nanomolar ("nM"). The relative contribution of BK channel-mediated current to total outward current was determined by subtraction of the current remaining in the presence of IBTX (non-BK current) from the current profiles obtained in all other experimental conditions (control, drug, and wash) [Gribkoff, V. K. et al., Mol. Pharmacol., 50:206–217 (1996)]. It was determined that at the tested concentrations the compounds profiled did not significantly effect non-BK native currents in the oocytes. All compounds were tested in 5–10 oocytes and are reported at the indicated concentration of 10 micromolar ("μM"); the effect of the selected compounds of the invention on BK current was expressed as the percent of control IBTX-sensitive current at a single transmembrane voltage (+140 mV) and is listed in Table 1. Recordings were accomplished using standard two-electrode voltage clamp techniques [Stuhmer, W., et al., Methods in Enzymology, Vol. 207: 319–339 (1992)]; voltage-clamp protocols consisted of 500–750 milliseconds ("ms") duration step depolarizations, from a holding potential of −60 mV, to a final voltage up to +140 mV in 20 mV steps. Table 2 lists the current-voltage (I-V) data for two compounds of the invention, applied to oocytes at a concentration of 10 μM. The experimental media (modified Barth's solution) consisted of millimolar ("mM"): NaCl (88), $NaHCO_3$ (2.4), KCl (1.0), HEPES (10), $MgSO_4$ (0.82), $Ca(NO_3)_2$ (0.33), $CaCl_2$ (0.41); pH 7.5.

TABLE 1

| Example. No | BK Current* |
|---|---|
| 3-atropisomer A | 291.8 ± 26.8% |
| 3-atropisomer B | 213.9 ± 21.4% |
| 5-atropisomer A | 360.8 ± 29.6% |
| 5-atropisomer A | 183.6 ± 9.50% |

*at 10 μM expressed as percent increase over BK current in controls, voltage step to +140 mV

TABLE 2

| | Current (μA) | | | |
|---|---|---|---|---|
| Voltage (mV) | Control | Compound of Example 1 | Compound of Example 2 | IBTX |
| −40 | 0 | 0 | 0 | 0 |
| −20 | 0 | 0 | 0 | 0 |
| 0 | 0 | 0.2 | 0 | 0 |
| 20 | 0 | 0.7 | 0 | 0 |
| 40 | 0 | 1.8 | 0.2 | 0 |
| 60 | 0 | 3.3 | 0.6 | 0 |
| 80 | 0.3 | 4.9 | 1.4 | 0.1 |
| 100 | 1.0 | 6.6 | 2.5 | 0.2 |
| 120 | 2.5 | 8.4 | 3.9 | 0.6 |
| 140 | 3.9 | 10.2 | 5.6 | 1.2 |

The compounds of the present invention are useful for the treatment of patients for conditions arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, sexual dysfunction, urinary incontinence and especially male erectile dysfunction, other disorders sensitive to BK channel activating activity. Accordingly, in one aspect of the present invention, there is provided a method of treatment or prevention of conditions responsive to opening of potassium channels in a patient in need thereof, which comprises administering to the patient a therapeutically effective amount of a compound of Formula I or a pharmaceutically acceptable salt, solvate or prodrug thereof. In another aspect, this invention provides a method for the treatment of or protection from disorders which are mediated by opening of the large conductance calcium-activated $K^+$ channels in a patient in need thereof, which comprises administering to the patient a therapeutically effective amount of a compound of Formula I or a pharmaceutically acceptable salt, solvate or prodrug thereof. Preferably, the compounds of Formula I are useful in the treatment of ischemia, stroke, convulsions, asthma, irritable bowel syndrome, migraine, traumatic brain injury, urinary incontinence, and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity.

In another aspect, this invention provides pharmaceutical compositions comprising at least one compound of Formula I and a carrier.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 micrograms per kilogram (μg/kg) to 50 milligrams per kilogram (mg/kg) body weight and preferrably, from about 0.1 μg/kg to 5 mg/kg body weight for oral administration. For parenteral administration, the dose may be in the range of 0.1 μg/kg to 1 mg/kg body weight for intravenous administration. The active ingredient will preferably be administered in equal doses from one to four times a day. However, usually a small dosage is administered, and the dosage is gradually increased until the optimal dosage for the host under treatment is determined.

The compounds of the present invention may be employed alone or in combination with other suitable therapeutic agents useful in the treatment of the dysfunction of cellular membrane polarization and conductance, e.g., sexual dysfunction such as cyclic guamine monophosphate, phosphodiaterase ("cGMP PDE") inhibitors and particularly cGMP PDE V inhibitors such as sildenafil. Exemplary of the therapeutic agents are PDE V inhibitors selected from imidazoquinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488,055), anthranilic acid derivatives (see WO 95/18097), fused heterocycles (see WO 98/07430) and thienopyrimidines (see DE 19632423). Alosetron hydrochloride can be combined with the compounds of the present invention to treat irritable bowel syndrome (see, e.g., U.S. Pat. Nos. 5,360,800 and 6,284,770).

The above therapeutic agents, when employed in combination with the compounds of the present invention, may be used, for example, in those amounts indicated in the Physician's Desk Reference (PDR) or as otherwise determined by one of ordinary skill in the art.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

EXAMPLES

The following examples are given by way of illustration and are not to be construed as limiting the scope of the claims which follow.

In the following examples, all temperatures are given in degrees Centigrade. Melting points were recorded on a Gallenkamp capillary melting point apparatus are uncorrected. Proton magnetic resonance ($^1H$ NMR) spectra were recorded on a Bruker AC 300 or 500 megaHertz ("mHz") spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 $cm^{-1}$ to 400 $cm^{-1}$, calibrated to 1601 $cm^{-1}$ absorption of a polystyrene film and reported in reciprocal centimeters ($cm^{-1}$). Low resolution mass spectra (MS) and the apparent molecular weight ($MH^+$) or (M-H) was determined on a Finnigan TSQ 7000. LC-MS analysis were carried out on a Shimadzu instrument using a YMC C18 column (4.6×50 mm) employing a 4 or 8 min linear gradient of 0% to 100% solvent B in A (solvent A: 10% methanol, 90% water, 0.1% TFA; solvent B: 90% methanol, 10% water, 0.1% TFA) with UV detector set at 220 nm. The element analyses are reported as percent by weight. Unless otherwise indicated in the Specific Embodiments, $R^2$ and $R^4$ are H in the descriptive title of the Examples.

Example 1

4-(5-Chloro-2-hydroxyphenyl)-3-(2-hydroxyethyl)-6 (trifluoromethyl)-2(1H)-Quinolinone The compound above was prepared as described below.

Step A—3-(2-Hydroxyethyl)-4-hydroxy-6-chlorocoumarin

To a solution of γ-butyrolactone (15.5 g, 178.0 mmol) in THF (100 mL) at −78° C. was added a 1.0 M THF solution of LiHMDS (356 mL, 356 mmol), and the resulting mixture stirred at −78° C. for 1.5 hours. A solution of 5-chlorosalicylic methyl ester (16.6 g, 98% purity, 89.0 mmol) in THF (95 mL) was added. After stirring for 1 hour at 0° C., the mixture was warmed to room temperature overnight to ensure complete reaction. After cooling to 0° C., conc. HCl (12 N, 150 mL) was slowly added to bring the pH to 1. The reaction solution was stirred until HPLC analysis indicated the absence of the keto-ester intermediate. To the mixture was added 400 mL $CH_2Cl_2$ and 300 mL $H_2O$; the organic phase was separated and the aqueous layer was extracted with $CH_2Cl_2$ (100 mL). The organic layers were combined and dried over anhydrous $Na_2SO_4$, and the solvent was removed under reduced pressure to give a solid. Heptane (165 mL) was added to a solution of the solid in THF (290 mL) to crystallize the product. After cooling to 0–5° C. for about 3 hours, the product was isolated by filtration and washed with heptane. After drying in vacuo, a total of 13.9 g (66% yield) of the title compound as off-white crystals was obtained. m.p. 185–186° C.; MS m/z 240;

$^1H$ NMR (DMSO-$d_6$, 300 MHz) δ 7.84 (d, 1H, J=2.4 Hz), 7.61 (dd, 1H, J=2.4, 8.8 Hz), 7.38 (d, 1H, J=8.8 Hz), 3.56 (t, 2H, J=6.6 Hz), 2.73 (t, 2H, J=6.6 Hz); $^{13}C$ NMR (DMSO-$d_6$, 75 MHz) δ 162.6, 159.9, 150.5, 131.4, 127.9, 122.4, 118.2, 117.8, 103.2, 59.4, 27.6; IR ($cm^{-1}$) 3247.2, 2945.1, 2458.6, 1664.9, 1623.9, 1572.7, 1311.5, 1378.1, 1070.8, 825.0.

| | | | |
|---|---|---|---|
| Anal. Calcd. for $C_{11}H_9O_4Cl$: | C, 54.90; | H, 3.77; | Cl, 14.73. |
| Found: | C, 54.79; | H, 3.70; | Cl, 14.76. |

Step B—2,3-Dihydro-8-chloro-4H-furobenzopyran-4-one

To a solution of 3-(2-hydroxyethyl)-4-hydroxy-6-chlorocoumarin (Example 1) (8 g, 33.3 mmol) in toluene (360 mL) at room temperature was added p-TSA (0.95 g, 5.0 mmol), and the resulting solution was refluxed with the removal of water using a Dean-Stark condenser. The reaction mixture was cooled to room temperature and washed with saturated sodium bicarbonate solution twice. Toluene was removed by atmospheric distillation to a final volume of 32 mL. After cooling to 70° C., the product started to crystallize. The crystal slurry was held between 55–65° C. for 30 minutes, followed by cooling to 0–5° C. The product was isolated by filtration, washed with cold toluene, and dried in vacuo. A total of 5.5 g (74% yield) of the title compound as off-white crystals was obtained. m.p. 144–146° C.; MS m/z 223 $(M+H)^+$;

$^1$H NMR ($CDCl_3$, 300 MHz) δ 7.58 (d, 1H, J=2.5 Hz), 7.49 (dd, 1H, J=2.3, 8.8 Hz), 7.30 (d, 1H, J=8.9 Hz), 4.90 (t, 2H, J=9.3 Hz), 3.21 (t, 2H, J=9.5 Hz); $^{13}$C NMR ($CDCl_3$, 75 MHz) δ166.4, 160.3, 153.4, 132.6, 129.6, 122.4, 118.6, 113.8, 103.6, 74.9, 27.1; IR ($cm^{-1}$) 3073.1, 2975.8, 1721.2, 1644.4, 1490.8, 1403.7, 1270.6, 1111.8, 1040.1.

| | | | |
|---|---|---|---|
| Anal. Calcd. for $C_{11}H_7O_3Cl$: | C, 59.35; | H, 3.17; | Cl, 15.92. |
| Found: | C, 59.13; | H, 3.16; | Cl, 15.93. |

Step C—4-(4'-Trifluoromethylphenylcarboxamide)-5-(2-hydroxy-5-chloro)-2,3-dihydrofuran To a solution of 2,3-dihydro-8-chloro-4H-furobenzopyran-4-one (Example 2) (1.02 g, 4.58 mmol) and 4-(trifluoromethyl)aniline (0.74 g, 4.58 mmol) in THF (50 mL) at −15° C. was added LiHMDS (10.5 mL, 10.5 mmol, 1.0M solution in THF). The clear, red solution was stirred at −15° C. until HPLC analysis indicated <1% of starting material remained (approximately 30 minutes). The reaction mixture was quenched by the addition of an aqueous solution of $NaH_2PO_4$ (50 mL, 10 wt % in $H_2O$). After the addition of tert-butyl methyl ether (25 mL), the layers were separated and the rich organic phase washed successively with $NaH_2PO_4$ (50 mL, 10 wt % in $H_2O$) and saturated brine solution. After drying over $Na_2SO_4$, the solution was concentrated to give the title compound as a clear, orange oil (1.76 g, 100% yield) which crystallized upon refrigeration. Addition of dichloromethane (20 mL) gave white crystals, which were isolated by filtration, washed with dichloromethane (10 mL) and dried to give 1.6 grams of the title compound (90% yield). m.p. 180–180.5° C.; MS m/z 384 $(M+H)^+$;

$^1$H NMR (DMSO-$d_6$, 300 MHz) δ 9.76 (s, 1H), 9.34 (s, 1H), 7.76 (d, 2H, J=8.5 Hz), 7.60 (d, 2H, J=8.7 Hz), 7.26 (s, 1H), 7.24 (dd, 1 H, J=2.2, 7.0 Hz), 6.83 (dd, $^1$H, J=2.4, 7.1), 4.52 (t, 2H, J=9.6 Hz), 3.16 (t, 2H, J=9.6 Hz); $^{13}$C NMR (DMSO-$d_6$, 75 MHz) δ 165.5, 159.7, 155.9, 144.7, 132.0, 131.3, 127.3, 123.7, 121.7, 121.2, 119.5, 110.1, 71.5, 32.9; IR ($cm^{-1}$) 3303.6, 2950.2, 1654.6, 1608.5, 1531.7, 1408.8, 1326.9, 1116.9, 1065.7, 840.4.

Step D—4-(5-Chloro-2-hydroxyphenyl)-3-(2-hydroxyethyl)-6 (trifluoromethyl)-2(1H)-quinolinone A solution of 4-(4'-trifluoromethylphenylcarboxamide)-5-(2-hydroxy-5-chloro)-2,3-dihydrofuran prepared in Example 3 (1.76 g, 4.58 mmol) in MeOH (500 mL) was purged with nitrogen and irradiated with a 450 W Hanovia lamp at 30–40° C. until HPLC analysis indicated <1% of compound (Example 3) remained. The MeOH was then concentrated in vacuo, and the resulting oil dissolved in dichloromethane (50 mL). Crystals formed after stirring for one hour at room temperature. After cooling the slurry to 0 ° C., the crystals were isolated by filtration and dried. A total of 0.54 g (30% yield) of the title compound was obtained as a crystalline solid with an HPLC purity of 97 area %. m.p. 253–255° C.; MS m/z 384 $(M+H)^+$.

$^1$H NMR (DMSO-$d_6$, 300 MHz) δ 12.27 (s, 1H), 9.91 (s, 1H), 7.79 (d, 1H, J=8.3 Hz), 7.53 (d, 1H, J=8.5 Hz), 7.42 (dd, 1 H, J=2.4, 8.6 Hz), 7.26 (d, 1H, J=2.4 Hz), 7.08 (s, 1H), 7.06 (d, 1H, J=8.9 Hz), 4.60 (m, 1H), 3.44 (m, 2H), 2.50 (m, 2H); $^{13}$C NMR (DMSO-$d_6$, 75 MHz) δ 163.7, 155.1, 145.9, 141.7, 132.6, 131.5, 131.3, 127.8, 127.4,125.5, 124.5, 123.5, 121.0, 119.3, 117.9, 60.7, 33.9.

The compound made in Example 1 is a racemic mixture of the (−) atropisomer and the (+) atropisomer, which are represented structurally in FIG. 1. The compound of Example I was subject to chiral chromatography. The chromatogram of the racemic mixture as well as individual atropoisomers are shown in FIGS. 1, 2, 3 and 4, respectively.

Example 2

4-(5-Chloro-2-hydroxyphenyl)-1-methyl-3-(2-hydroxyethyl)-6-trifluoromethyl)-2(1H)-quinolinone The compound above was prepared as described below.

Step A:—Acetic acid 2-{3-[2-(tert-butyl-diphenyl-silanyloxy)-ethyl]-2-oxo-6-trifluoromethyl-1,2-dihydro-quinolin-4-yl}-4-chloro-phenyl ester To a solution of the compound of Example 1 (5.00 g, 13.0 mmol) in dry DMF (100 mL) was added tert-butyldiphenylsilyl chloride (10.74 g, 39.1 mmol) and imidazole (2.66 g, 39.1 mmol) at ambient temperature under argon. The reaction mixture was stirred for 3 hours and diluted with ethyl acetate (300 mL). The organic layer was washed with water (2×100 mL), brine (100 mL) and dried. Solvent was evaporated to obtain the silyl ether (6.61 g, 10.63 mmol, 81%). To the solution of the silyl ether in dry dichloromethane (200 mL) was added $Ac_2O$ (5.43 g, 53.2 mmol) and $Et_3N$ (5.38 g, 53.2 mmol) at room temperature under argon. The reaction mixture was stirred for 4 hours and the mixture was diluted with ethyl acetate (200 mL). The organic mixture was washed with water (2×100 mL), brine (100 mL) and dried. The solvent was then evaporated. Purification was conducted by column chromatography ($SiO_2$) using hexane, ethyl acetate (95:5 to 80:20) as eluent to afford the compound of Step A (6.82 g, 96%, retention time, "$R_t$",=2.3 minutes on a $C_{18}$ liquid chromatography, "$C_{18}$ LC" column) as a white solid. MS [M+H]=664. $^1$H NMR ($CD_3OD$) δ 7.74 (d, J=7.6 Hz, 1H), 7.60 (d, J=6.2 Hz, 1H), 7.52 (m, 5H), 7.37 (m, 2H), 7.31 (m, 5H), 7.23 (s, 1H), 7.17 (s, 1H), 3.94 (m, 1H), 3.80 (m, 1H), 2.89 (m, 1H), 2.72 (m, 1H), 1.76 (s, 3H), 0.97 (s, 9H).

Step B:—Acetic acid 2-{3-[2-(tert-butyl-diphenyl-silanyloxy)-ethyl]-1-methyl-2-oxo-6-trifluoromethyl-1,2-dihydro-quinolin-4-yl}-4-chloro-phenyl ester A suspension of the product from step A (6.82 g, 10.3 mmol), methyl iodide (4.37 g, 30.8 mmol) and $K_2CO_3$ (3.05 g, 30.8 mmol) in acetone (200 mL) at ambient temperature was stirred for 18 hours. At the end diluted with ethyl acetate (200 mL), washed with water (100 mL), brine (100 mL) and dried. Chromatography with gradient elution ($SiO_2$) using hexanes, ethyl acetate (90:10 to 70:30) afforded the compound of Step B as the major product (5.52 g, 8.1 mmol, 79%, $R_t$=2.3 minutes $C_{18}$ LC) as white solid. MS [M+H]=678. $^1$H NMR ($CD_3OD$) δ 7.82 (d, J=8.1 Hz, 1H), 7.73 (d, J=8.9 Hz, 1H), 7.52 (d, J=9.2 Hz, 1H), 7.48 (m, 4H), 7.34 (m, 3H), 7.21 (m, 6H), 3.91 (m, 1H), 3.76 (m, 4H), 2.88 (m, 1H), 2.70 (m, 1H), 1.71 (s, 3H), 0.94 (s, 9H). A minor product characterized as the O-methyl derivative had the following characteristics. MS [M+H]=678. $^1$H NMR ($CD_3OD$) δ 7.82 (d, J=8.1 Hz, 1H), 7.95 (d, J=5.1 Hz, 1H), 7.52 (d, J=9.2 Hz, 1H), 7.48 (m, 4H), 7.34 (m, 3H), 7.21 (m, 6H), 3.91 (m, 1H), 3.76 (m, 4H), 2.88 (m, 1H), 2.70 (m, 1H), 1.71 (s, 3H), 0.94 (s, 9H). The ratio of the N-methyl derivative to the O-methyl derivative was approximately 9:1.

Figure 5:
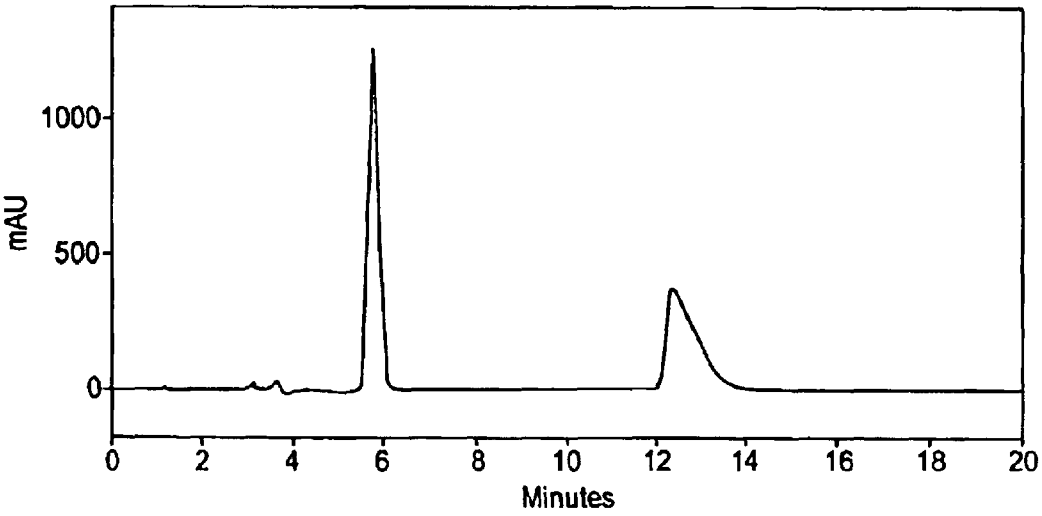
FIG. 5 is an HPLC chromatogram of a racemic mixture of the atropisomers in accordance with the present invention.
Figure 6:
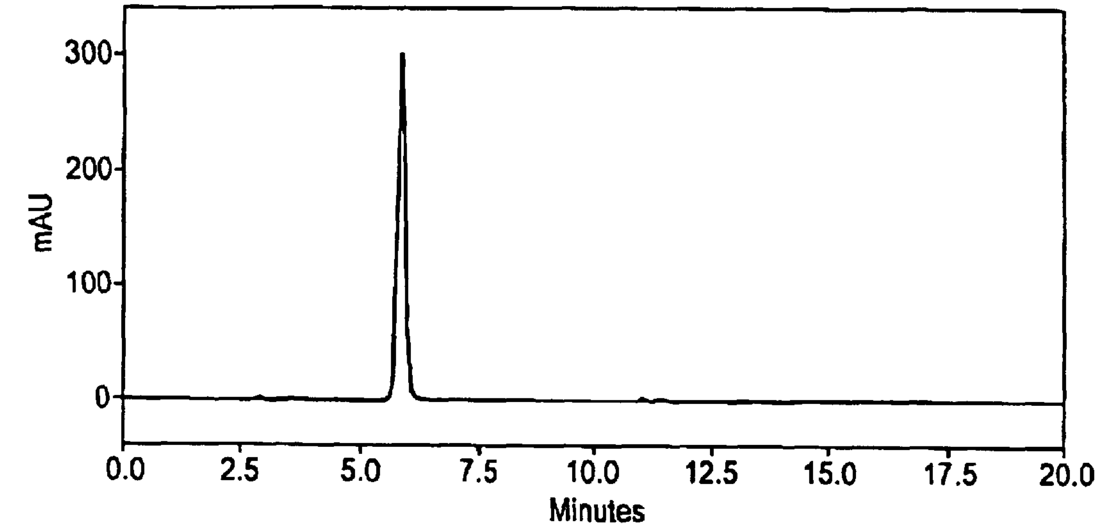
FIG. 6 is an HPLC chromatogram of an atropisomer in accordance with the present invention.
Figure 7:
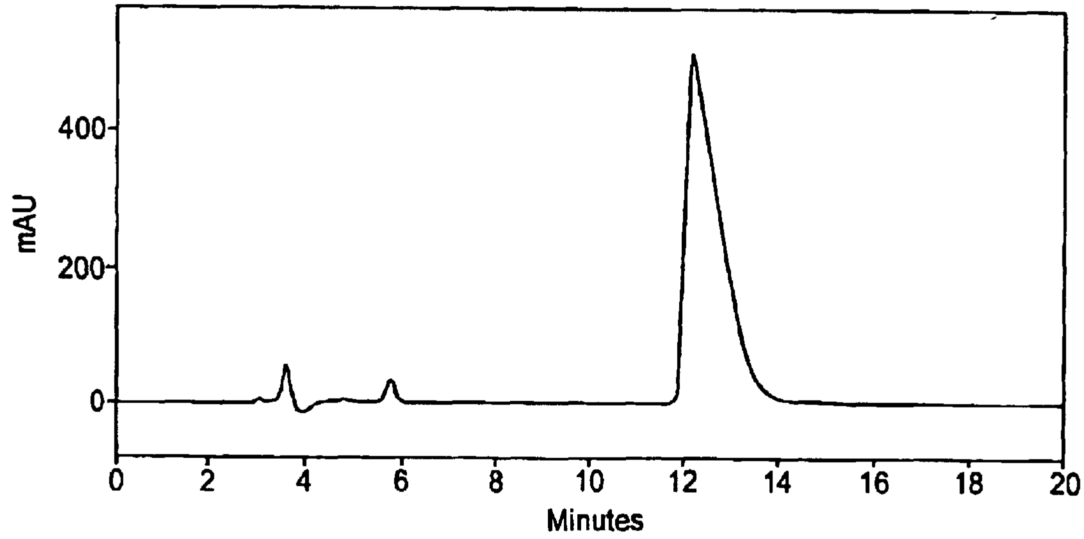
FIG. 7 is an HPLC chromtoagram of an atropisomer in accordance with the present invention.

Step C: —4-(5-Chloro-2-hydroxyphenyl)-1-methyl-3-(2-hydroxyethyl)-6-trifluoromethyl )-2(1H)-quinolinone The acetyl silyl ether (760 mg, 1.12 mmol) was stirred with $LiOH.H_2O$ (320 mg) in EtOH (10 mL) for 18 hours at ambient temperature. At the end volatiles were removed in vacuo. The residue was dissolved in THF (5 mL) and treated with tera-n-butylammonium fluoride (1M in THF, 3 equivalents). After stirring for 18 hours an additional 3 equivalents was added and stirred for another 18 hours. THF was evaporated, partitioned between EtOAc water. Organic layer dried ($Na_2SO_4$), evaporated in vacuo. The residue was purified by silica gel column chromatography with EtOAC : $CH_2Cl_2$ (3:2) as eluant. Fractions containing required compound were combined and evaporated in vacuo to give 290 mg (65% yield) of the required product. Recrystallization from EtOAc and hexane gave 152 mg of the N-methyl derivative. $^1$H NMR (500 MHz, DMSO-$d_6$): δ2.56 (2H, m), 3.40 (2H, m), 3.75 (3H, s), 4.57 (1 H, m), 7.05 (1H, d, J=8.8), 7.14 (1H, s), 7.25 (1H, d, J=2.6), 7.41 (1H, dd, J=8.7, 2.7), 7.77 (1H, d, J=8.8), 7.89 (1H, dd, J=8.8, 2.0), 9.91 (1H, s); MS m/e 398 ($MH^+$). The compound of Example 2 was subjected to chiral chromatography. The chromatograms of the racemic mixture and the individual atropisomers are shown in FIGS. 5, 6 and 7, respectively.

Example 3

Resolution of Atropisomers from Example 1

Figure 2:
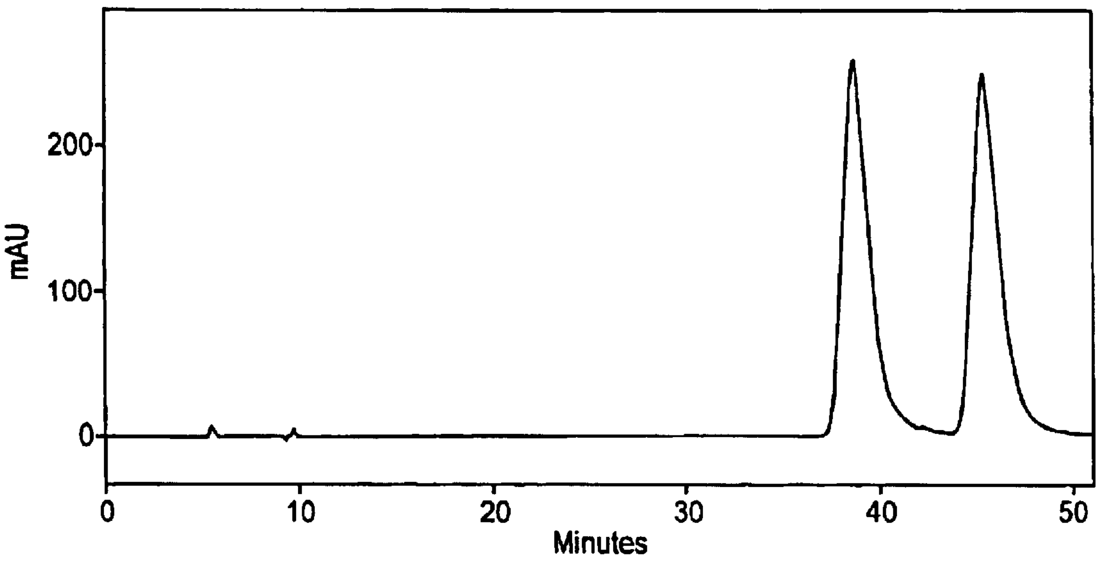
FIG. 2 is an HPLC chromatogram of a racemic mixture of the atropisomers in accordance with the present invention.

(−) 4-(5-Chloro-2-hydroxy-phenyl)-3-(2-hydroxy-ethyl)-6-trifluoromethyl-1H-quinolin2-one (+) 4-(5-Chloro-2-hydroxy-phenyl)-3-(2-hydroxy-ethyl)-6-trifluoromethyl-1H-quinolin2-one A solution of 1 (~50 mg) in i-PrOH: hexane (1:1, 2 mL) was applied in four injections on to a ChiralPak AD, 21×250 mm, 10 μm particle size column in four injections. Elution with i-PrOH: hexane (1:19) was carried out at a flow rate of 10 mL/min. Detector $UV_{max}$ at 234 nm was employed. The fraction containing the faster moving isomer, isomer A, ($t_R$=46.1 min) upon evaporation gave 20 mg, while the fraction containing later peak ($t_R$=48.3 min) upon evaporation provided 21 mg of isomer B. The chromatogram of the racemate is shown in FIG. 2.

Characterization of Atropisomer A (−): The $^1$H NMR and $^{13}$C NMR spectra were indistinguishable from those shown for the racemate in Example 1. Optical rotation for isomer A was determined in MeOH,. $[\alpha]^{22}_D$ (meOH)=−8.8°.

Characterization of Atropisomer B (+): The $^1$H NMR and $^{13}$C NMR spectra were indistinguishable from those reported for the racemate in Example 1. Optical rotation for isomer B was determined in MeOH, $[\alpha]^{22}_D$ (meOH)=+9.6°.

Figure 3:
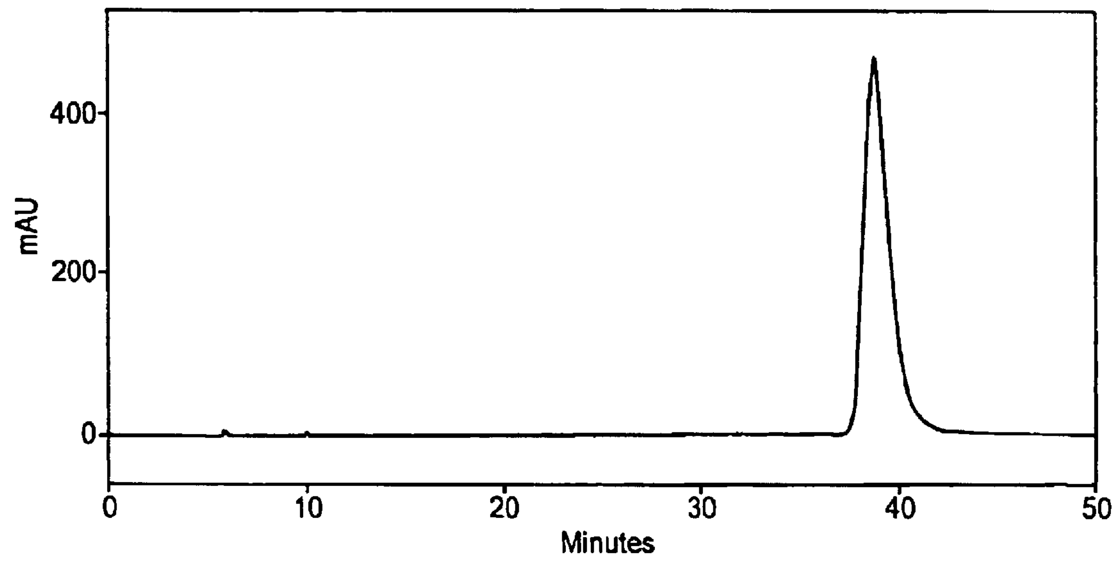
FIG. 3 is an HPLC chromatogram of an atropisomer in accordance with the present invention.
Figure 4:
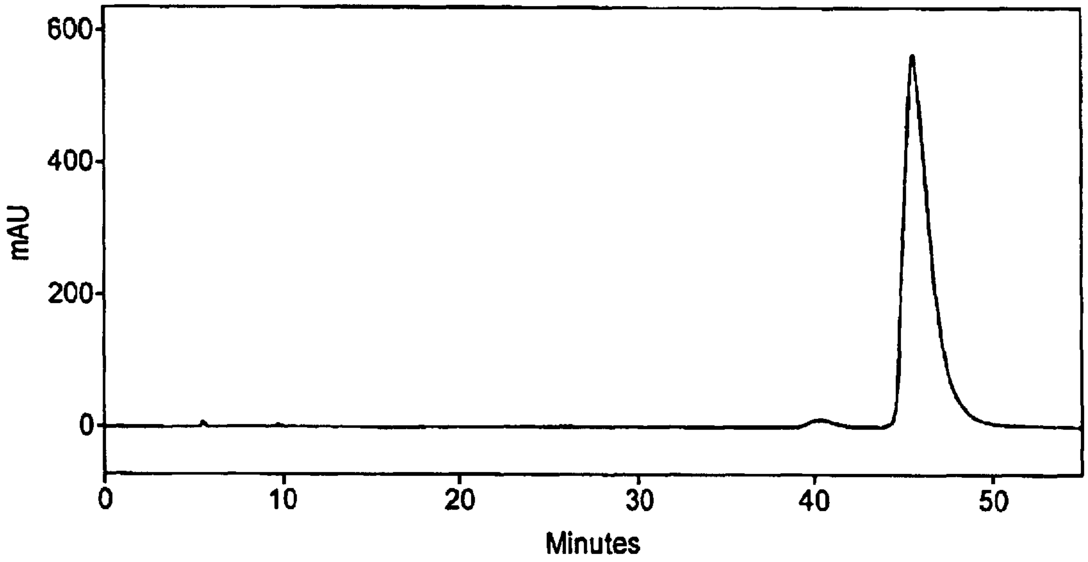
FIG. 4 is an HPLC chromtoagram of an atropisomer in accordance with the present invention.

The resolved atropisomers were subjected to reverse phase HPLC as described above with respect to the racemate. The chromatograms for each atropisomer are shown in FIGS. 3 and 4.

Example 4

Stability of Atropisomers from Example 3

Chiral HPLC studies: Ethanol solutions (~3 mg/mL) of the two atropoisomers of Example 1 were stored at room temperature and were examined by chiral HPLC as described above on chiralpak AD column for racemization. The two compounds were found to be stable even after a month at ambient temperature. No appreciable racemization was observed.

Example 5

Resolution of Atropisomers from Example 2

(−) 4-(5-Chloro-2-hydroxy-phenyl)-1-methyl-3-(2-hydroxy-ethyl)-6-trifluoromethyl-1H-quinolin2-one (+) 4-(5-Chloro-2-hydroxy-phenyl)-1-methyl-3-(2-hydroxy-ethyl)-6-trifluoromethyl-1H-quinolin2-one The racemate was separated as described in Example 3 on Chiralpak AD column, 4.6×250mm, 10 μm with 2-propanol:hexane:trifluroacetic acid (1600:399:1). The faster eluting isomer ($t_R$=8.5 min) was designated as isomer A and the slower one ($t_R$=19.0 min) as isomer B. The chromatogram of the racemate is shown in FIG. 5.

Characterization of Isomer A (−): The $^1$H NMR spectrum is indistinguishable from those reported for the racemate in Example 2. Optical rotation for isomer A was determined in MeoH., $[\alpha]^{22}_D$(MeOH)=−6.9°.

Characterization of Isomer B (+): The $^1$H NMR spectrum is indistinguishable from those reported for the racemate in Example 2. Optical rotation for isomer A was determined in MeoH., $[\alpha]^{22D}$(MeOH)=+5.0°.

The resolved atropisomers were subjected to chiral HPLC as described above with respect to the racemate. The chromatograms are shown in FIGS. 6 and 7.

Example 6

Air Jet Stress-Induced Colonic Motor Activity

Environmental stress is believed to play a role in irritable bowel syndrome and other altered bowel motility states. In animal models, environmental stress has been shown to cause an increased defecatory response, presumably, a result of increased entero-motor activity. Based on this, we tested the hypothesis that maxi-$K^+$potassium channel openers of the present invention can be effective in reducing stress-induced acceleration in colonic motility, as indexed by fecal pellet output.

Rats were randomly divided into 2 groups and treated with vehicle (polyethylene glycol (400 grams per mole), 1 mL/kg, ip) or the compound of Example 1 in racemate form (20 mg/kg) at time zero. At 1.5 hr post-treatment, each rat was partially restrained in plexiglas container and was subjected to air-jet stress. This was brought about by exposing each of the partially-restrained animals to 3–4 episodes of 2 minute long air jets with an interval of 8–10 minutes between episodes. The fecal output was collected and the wet weight was recorded. The data were analyzed by combining individual output within each group to calculate a group mean and the means were compared using a statistical test (unpaired, two-tailed t-test; $p<0.05$).

The fecal output of the vehicle treated group was 0.37 grams and the fecal output of the compound treated group was 0.03 grams. The animals in the vehicle-treated group overwhelmingly (9/12) showed a defecatory response to air-jet. In contrast, only 3 out of 11 compound treated animals showed a defecatory response. The mean fecal output of this group was markedly less than the vehicle-treated group mean.

It was found that the compounds of the present invention can significantly attenuate stress-induced colonic motility in rats.

The results of the above biological tests demonstrate that the compounds of the invention can be potent openers of the large-conductance calcium-activated $K^+$channels (Maxi-K or BK channels). In addition, it has been found that the atropisomers have different activities.

Although the invention has been described with respect to specific aspects, those skilled in the art will recognize that other aspects are intended to be included within the scope of the claims which follow. For example, reaction schemes other than the ones specifically described can be used to make the atropisomers. Also, other substituents substantially equivalent to the specific substituents described herein, e.g., R, $R^1$, $R^2$, $R^3$, $R^4$, $R^5$, can be employed within the scope of the invention. Furthermore, all documents cited in this application, e.g., patents and publications, are incorporated by reference.

What is claimed is:

1. An atropismoer of the formula

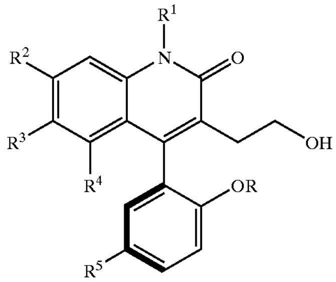

wherein

R and $R^1$ each are independently hydrogen or methyl;

$R^2$, $R^3$ and $R^4$ each are independently hydrogen, halogen, nitro or trifluoromethyl, provided $R^2$, $R^3$, and $R^4$ are not all hydrogen; and $R^5$ is bromo, chloro or nitro; or a nontoxic pharmaceutically acceptable salt, solvate or prodrug thereof.

2. The atropisomer of claim 1 substanitally free of its corresponding atropisomer of the formula

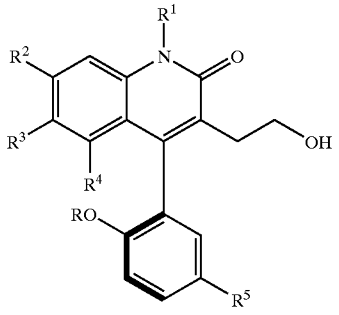

wherein R, $R^1$, $R^2$, $R^3$, $R^4$ and $R^5$ are defined in claim 1.

3. The atropisomer of claim 1 wherein $R^1$ is hydrogen.

4. The atropisomer of claim 1 wherein $R^1$ is methyl.

5. The atropisomer of claim 1 which is stable for at least about 1 day.

6. An atropisomer of the formula

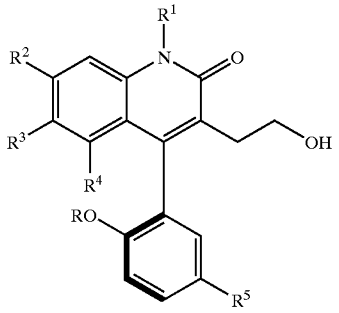

wherein

R and $R^1$ each are independently hydrogen or methyl;

$R^2$, $R^3$ and $R^4$ each are independently hydrogen, halogen, nitro or trifluoromethyl, provided $R^2$, $R^3$, and $R^4$ are not all hydrogen; and $R^5$ is bromo, chloro or nitro; or a nontoxic pharmaceutically acceptable salt, solvate or prodrug thereof.

7. The atropisomer of claim 6 substanitally free of its corresponding atropisomer of the formula

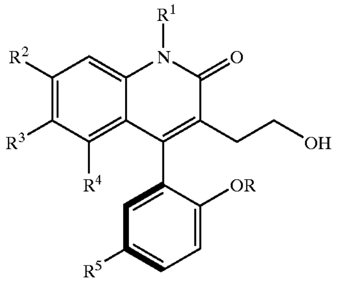

wherein R, $R^1$, $R^2$, $R^3$, $R^4$ and $R^5$ are defined in claim 6.

8. The atropisomer of claim 6 wherein $R^1$ is hydrogen.

9. The atropisomer of claim 6 wherein $R^1$ is methyl.

10. The atropisomer of claim 6 which is stable for a period of at least about 1 day.

11. A composition comprising the compound of claim 1, or a pharmaceutically acceptable salt or solvate thereof, and a pharmaceutically acceptable carrier.

12. The pharmaceutical composition of claim 11 comprising a therapeutically effective amount of the compound for the treatment of conditions responsive to openers of large conductance calcium-activated potassium channels.

13. A method of treating a condition selected from the group consisting of ischemia, stroke, convulsions, epilepsy, asthma, irritable bowel syndrome, migraine, traumatic brain injury, spinal cord injury, sexual dysfunction and urinary incontinence in a mammal which comprises administering to said mammal a therapeutically effective amount of the compound of claim 1.

14. A method for treating a condition which comprises administering to a mammal in need thereof a therapeutically effective amount of the compound of claim 1 wherein the condition is selected from the group consisting of ischemia, stroke, convulsions, epilepsy, asthma, irritable bowel syndrome, migraine, traumatic brain injury, spinal cord injury, sexual dysfunction and urinary incontinence.

15. The method of claim 14 wherein the condition is irritable bowel syndrome.

16. The method of claim 14 wherein the condition is sexual dysfunction.

17. A composition comprising the compound of claim 6 or a pharmaceutically acceptable salt or solvate thereof, and a pharmaceutically acceptable carrier.

18. A method of treating a condition selected from the group consisting of ischemia, stroke, convulsions, epilepsy, asthma, irritable bowel syndrome, migraine, traumatic brain injury, spinal cord injury, sexual dysfunction and urinary incontinence in a mammal which comprises administering to said mammal a therapeutically effective amount of the compound of claim 6.

19. The method of claim 18 wherein the condition is irritable bowel syndrome.

20. The method of claim 18 wherein the condition is sexual dysfunction.

* * * * *